US00PP11075P

United States Patent [19]

Hanes

[11] Patent Number: Plant 11,075

[45] Date of Patent: Oct. 5, 1999

[54] GERANIUM PLANT NAMED 'AMRI VIO'

[75] Inventor: Mitchell Eugene Hanes, Morgan Hill, Calif.

[73] Assignee: Goldsmith Seeds, Inc., Gilroy, Calif.

[21] Appl. No.: 08/974,102

[22] Filed: Nov. 19, 1997

[51] Int. Cl.[6] ..... A01H 5/00

[52] U.S. Cl. ..... Plt./329

[58] Field of Search ..... Plt./87.12, 325, Plt./328, 329

[56] References Cited

PUBLICATIONS

UPOV CD–ROM, Geranium plant named 'Amrio New Vio', PBR 97–1092, Canada, 1997.

*Primary Examiner*—Howard J. Locker
*Assistant Examiner*—Melissa L. Kimball
*Attorney, Agent, or Firm*—Rothwell, Figg, Ernst & Kurz

[57] ABSTRACT

A new geranium cultivar particularly distinguished by green foliage, violet flower color, and semi-double flowers on large umbels, fast rooting and a branching growth habit.

2 Drawing Sheets

BACKGROUND OF THE NEW PLANT

The present invention comprises a new and distinct cultivar of geranium, botanically known as *Pelargonium hortorum* Bailey, and hereinafter referred to by the cultivar name Amri Vio. The new cultivar is propagated from a seedling resulting from the cross of an experimentally produced seed parent known as 4773-1 and the pollen parent 4368-1. 'Amri Vio' is a product of a planned breeding program intended to create new geranium cultivars with violet colored flowers, semi-double flower form, dark green foliage, and improved superior cutting productivity. The new cultivar was created in 1994 in Gilroy, Calif. and has been repeatedly asexually reproduced by cuttings in Gilroy, Calif. and Guatemala over a three year period. It has also been trialed at Okemos, Mich. It has been found to retain its distinctive characteristics through successive propagations; and this novelty appears to be firmly fixed.

DESCRIPTION OF PHOTOGRAPH

This new geranium plant is illustrated by the accompanying photographs which show blooms, buds, and foliage of the plant in full color, the colors shown being as true as can be reasonably obtained by conventional photographic procedures.

Sheet 1 shows overall plant habit of 'Amri Vio'.

Sheet 2 shows a closer view of the flowers of 'Amri Vio'.

DESCRIPTION OF THE NEW CULTIVAR

The following detailed descriptions set forth the distinctive characteristics of 'Amri Vio'. The data which defines these characteristics were collected from asexual reproductions carried out by Goldsmith Seeds, Inc. in Gilroy, Calif. The palnt history was taken on 18 week old plants, blossomed under natural light in a greenhouse and color readings were taken in the greenhouse in Gilroy, Calif. on May 19, 1997 at 11 a.m. under ambient light. Color references are primarily to The R.H.S. Colour Chart of The Royal Horticultural Society of London (R.H.S.).

THE PLANT

Classification:

*Botanical.*—*Pelargonium hortorum* Bailey.

*Commercial.*—Zonal Geranium.

Form: Upright and somewhat open as a young plant.

Height: 13 to 15 cm, as a 4½ inch pot plant, excluding blooms.

Growth: Moderately vigorous growth with axillary bud breaks.

Outdoor plant performance: The plant exhibits good heat tolerance and strong growth, with a rounded growth habit when grown outdoors.

Foliage: Abundant quantity.

Stems: Green 146C R.H.S., internode length approximately 1.3–2.1 cm with the leaves arranged in an alternate leaf pattern.

Leaves:

*Size.*—Diameter about 7 cm.

*Shape.*—Rounded cordate with occasional up folding between veins.

*Margin.*—Irregularly crenate.

*Texture.*—Leathery and pubescent on both surfaces, especially along veins.

*Ribs and veins.*—Distinctly palmate, 3.5 to 4.5 cm long.

*Color.*—Upper side: Green 137B R.H.S. and without zonation. Under side: Green 146B R.H.S. Ribs and veins not prominently different from upper surface.

*Petioles.*—About 3.8 to 4.8 cm in length.

Disease resistance: None observed.

THE BUD

Size:

*Diameter.*—About 6 mm.

*Length.*—About 2.2 to 2.4 cm at time of bud opening.

Shape: Pointed ovoid.

Color: Petals when sepals first divide, 66B R.H.S.

Sepals: 5 in number, flat behind petals. Pointed linear lanceolate, 143C R.H.S. in an open flower.

THE FLOWER

Blooming habit: Continuous throughout the year.

Size: Approximately 4.9 cm in diameter, 1.5 cm deep, irregularly radially symmetrical.

Form: Cup-shaped when bloom first opens, later flattening to shallow cup shape with maturity.

Petals: 5 imbricate outer petals, 2.1–2.4 cm wide and approximately 2.4 cm long. Two to six inner smaller petaloids of varying shape. Both the outer petals and inner petaloids are violet 66A-B R.H.S. The base of the two upper outside petals each have an orange 30A R.H.S. blotch. The blotch is at the base of the petal and extends one third of the way up the petal. This blotch is present on the front and back of the petal. The veins are not significantly darker than the interveinal regions. Color changing little with age. Underside of petals lighter. Petals and petaloids soft and satiny.

Pedicel: Approximately 2.7 cm in length.

Persistance: An open flower will hold its petals until the flower begins to dehisce, approximately 7–10 days.

Fragrance: None.

INFLORESCENCE

Type: An umbel composed of approximately 35 flowers, erect or laterally ascending.

Peduncle: Approximately 12–13.5 cm in length. Green.

REPRODUCTIVE ORGANS

Stamens:

*Anthers.*—6–8 anthers positioned below the mature stigma, dull red prior to anthesis.

*Filaments.*—Most are white yet some have streaks of red pigmentation.

*Pollen.*—Orange in color.

Pistil:

*Number.*—1.

*Length.*—Approximately 8 mm.

*Stigma.*—5 linear lobes of near equal length, curling back toward ovary, purplish-red in color.

*Style.*—Length: About 4 mm. Color: Purplish red.

*Ovaries.*—At anthesis, densely pubescent with white hairs, oblong. Green drying to a light brown at maturity.

*Fruit.*—Partially fertile.

I claim:

1. A new and distinct cultivar of geranium plant substantially as herein shown and described, named Amri Vio, that is characterized by: green foliage, violet flower color, and semi-double flowers on large umbels, fast rooting and a branching growth habit.

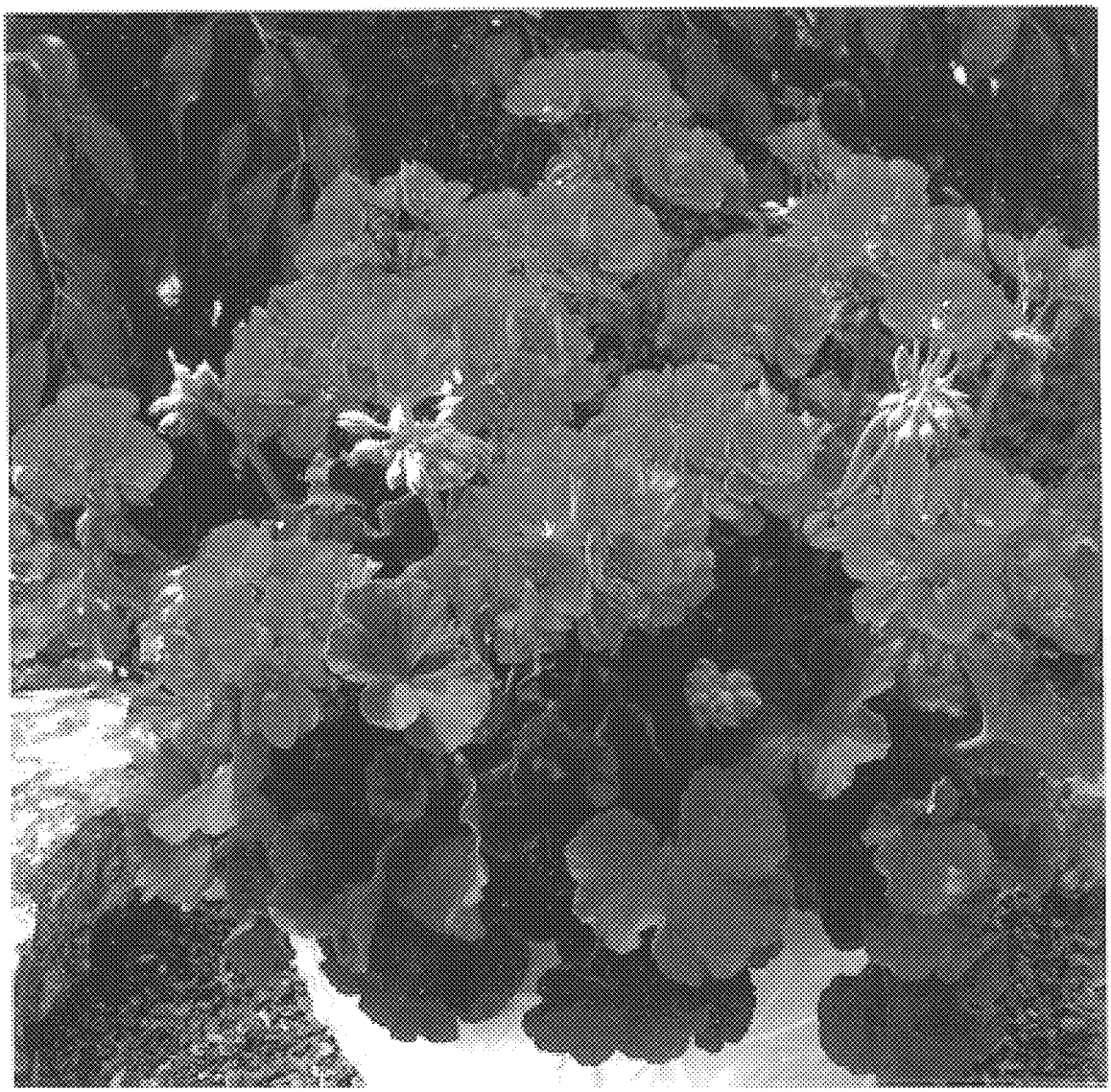

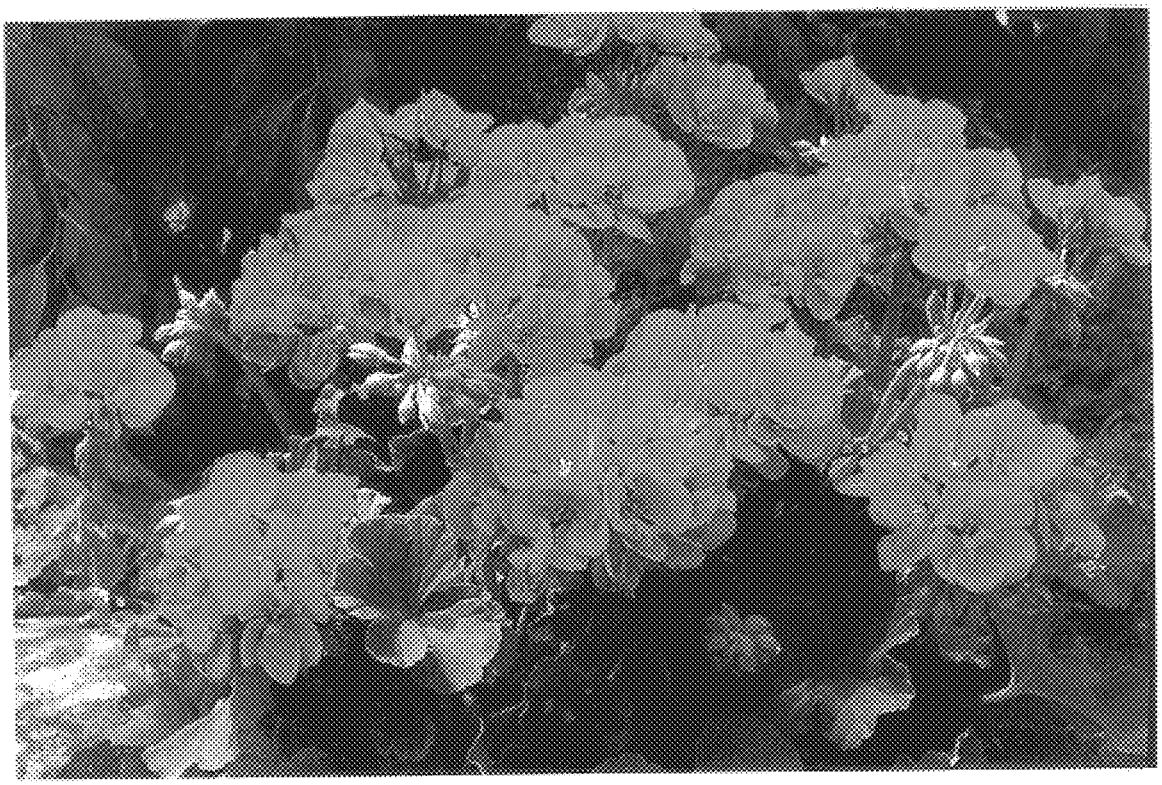

* * * * *